United States Patent [19]
Rometsch

[11] Patent Number: 5,570,694
[45] Date of Patent: Nov. 5, 1996

[54] BLOOD PRESSURE MEASURING DEVICE AND A METHOD OF CONTROLLING THE CUFF PRESSURE IN A BLOOD PRESSURE MEASURING DEVICE

[75] Inventor: Rainer Rometsch, Wildberg, Germany

[73] Assignee: Hewlett-Packard Company, Palo Alto, Calif.

[21] Appl. No.: 303,020

[22] Filed: Sep. 8, 1994

[30] Foreign Application Priority Data

Sep. 16, 1993 [DE] Germany ............................ 43 31 451.1

[51] Int. Cl.⁶ ................................................................. A61B 5/02
[52] U.S. Cl. ......................... 128/680; 128/685; 137/487.5
[58] Field of Search ............................... 128/672, 680–6; 606/202; 137/487.5

[56] References Cited

U.S. PATENT DOCUMENTS

4,510,940  4/1985  Wesseling ............................ 128/681
4,543,962  10/1985  Medero et al. .
5,052,397  10/1991  Ramsey, III et al. .
5,137,026  8/1992  Waterson et al. .

*Primary Examiner*—Angela D. Sykes
*Assistant Examiner*—Bryan Yarnell

[57] ABSTRACT

For controlling the cuff pressure in a blood pressure measuring device, the volume flow between a pump for filling the cuff and a valve for emptying the cuff on the one hand and the cuff on the other hand is detected by a flow sensor whose output signal is integrated by means of an integration circuit for producing an actual volume value. A computer unit for controlling the pump and the valve produces the control signals on the basis of this volume value formed by integration as well as on the basis of at least one quantity representative of the pressure/volume dependence of the cuff pressure.

18 Claims, 9 Drawing Sheets

BLOOD PRESSURE MEASURING DEVICE AND A METHOD OF CONTROLLING THE CUFF PRESSURE IN A BLOOD PRESSURE MEASURING DEVICE

FIELD OF THE INVENTION

The present invention deals with a blood pressure measuring device and with a method of controlling the cuff pressure in a blood pressure measuring device. Especially, but not exclusively, the present invention refers to a blood pressure measuring device permitting a more precise automatic adjustment of the cuff pressure.

DESCRIPTION OF THE PRIOR ART

Known blood pressure measuring devices, in which a cuff filled with air is used for determining the blood pressure values, operate in accordance with a corresponding method for adjusting the cuff pressure. According to this method, the cuff if first filled, e.g. by actuating a pump, until the cuff pressure value is higher than the systolic pressure. Subsequently, a controlled cuff-venting operation is carried out; in this operation, the cuff pressure normally is to be controlled in an ideal manner in such a way that it is lowered in the form of predetermined pressure steps, one measured value or a plurality of measured values being typically detected at each pressure step. The measuring process itself or rather the course of action for determining the blood pressure value itself can be performed in different ways.

Automatic blood pressure measuring devices typically measure the oscillations, induced in the cuff by the artery, during continuous or stepwise venting of the cuff or during the cuff-filling operation.

The oscillations, which are induced in the cuff by the pulsating blood in the artery, are normally detected by means of a pressure sensor detecting the cuff air pressure.

Deviating from the above, the detection and evaluation of the blood pressure can be carried out in a similar method of filling and continuously venting the cuff by means of a microphone which is arranged in the cuff and which detects the socalled Korotkov noise.

These known blood pressure measuring devices all show the feature that a pressure signal, which is produced by a pressure sensor and which is intended to be representative of the condition of the pneumatic system, is used for controlling the filling operation and the venting operation. Normally, this pressure sensor is accommodated in the blood pressure measuring device, but not in the area of the cuff. This structural feature of know blood pressure measuring devices and the consequences resulting therefrom with regard to the mode of operation and the measuring method will be explained hereinbelow with regard to FIG. 9, which shows a known blood pressure measuring device.

Figure 9:
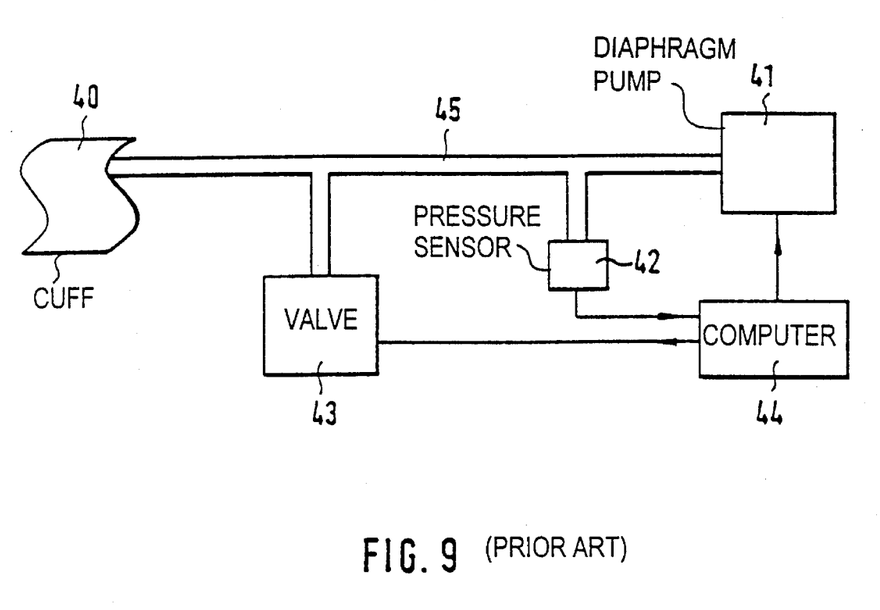
FIG. 9 is a block diagram of the known blood pressure measuring device.

As can be seen in FIG. 9, such an automatic blood pressure measuring device comprises a cuff 40, which can, for example, be wrapped around a patient's arm, a pressure generation device 41 used for filling the cuff 40 and constructed e.g. as a diaphragm pump, a pressure sensor 42 for generating a pressure signal representative of the cuff pressure as well as a valve 43 used for controlled venting of the cuff 40. The valve 43, the pressure sensor 42 and the pressure generation device 41 are connected to a control unit 44, which serves to control the cuff-filling operation and the cuff-venting operation on the basis of the pressure signal supplied by the pressure sensor 42.

Depending on requirements and safety standards, additional valves for venting or other venting mechanisms can be added. In view of the fact that these elements are, however, not essential with regard to the fundamental mode of operation of the known pressure sensor device, they are not shown in FIG. 9. The pressure generation device 41, the pressure sensor 42, the valve 43 as well as the cuff 44 are interconnected by a system of flexible tubes 45.

As is already clearly evident from the graphic representation according to FIG. 9, the measuring point for detecting the pressure in the cuff 40 is located close to the pressure generation device 41 and, consequently, it is separated from said cuff 40 by almost the entire length of the system of flexible tubes 45. In other words, the pressure is measured close to the valve 43 and the pressure generation device 41. During the cuff-filling and venting operations as well as quite generally during flow processes within the system of flexible tubes 45, pressure drops will occur within the system of flexible tubes 45 as well as at couplings (not shown) between the cuff 40 and the measuring point at which the pressure sensor 42 is arranged. As will be explained in detail hereinbelow, the pressure value detected by the pressure sensor 42 is superimposed by dynamic disturbances and indicates the real pressure within the cuff 40 only in the steady-state condition after the termination of flow processes.

Figure 10:
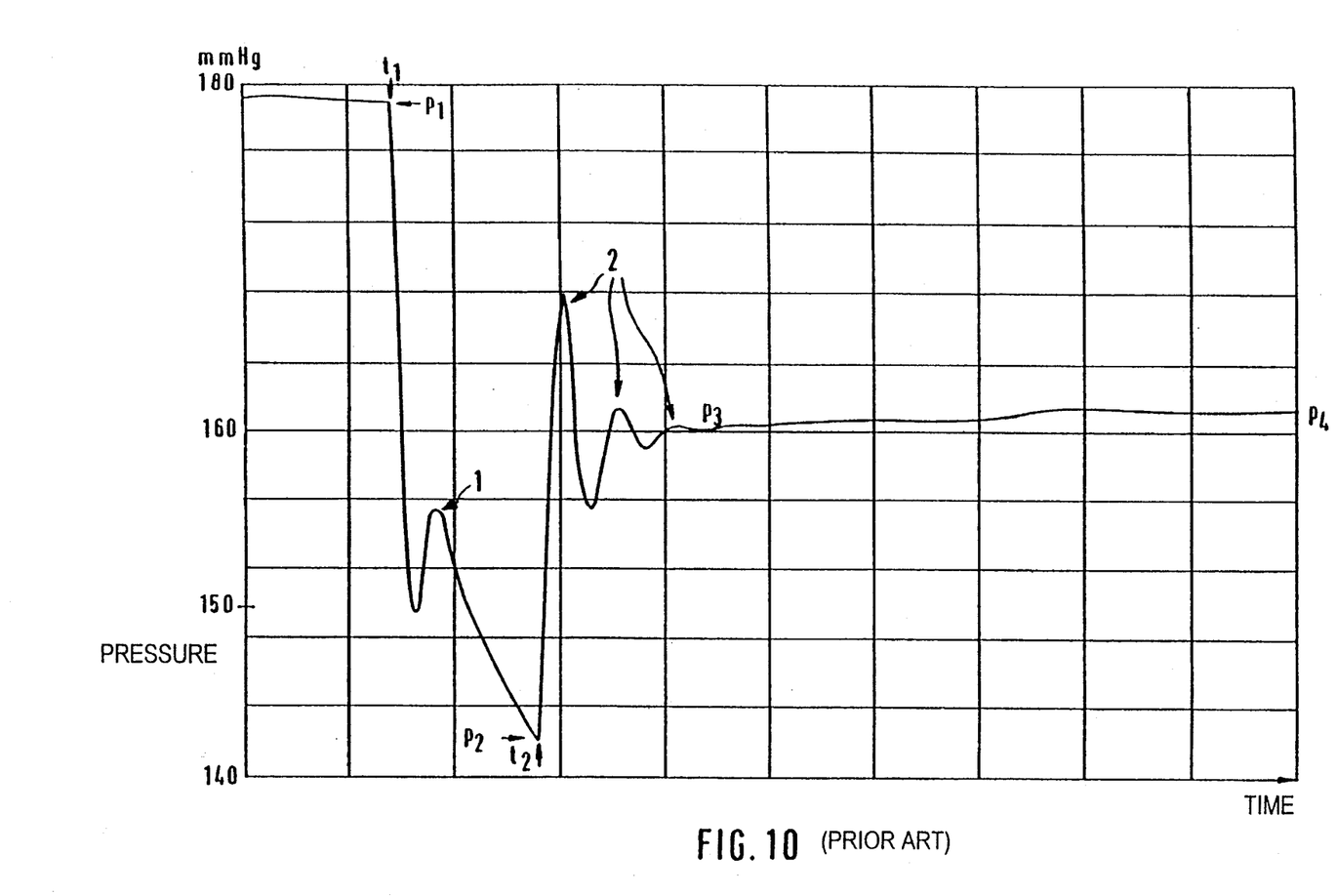
FIG. 10 is a plot of the variation with time of the cuff pressure as detected by the pressure sensor of the blood pressure measuring device in the known blood pressure measuring device according to FIG. 9.

FIG. 10 shows the pressure characteristic at a venting step of the stepwise venting process, said pressure characteristic being detected by the pressure sensor 42 in the system shown in FIG. 9.

Initially, the pressure p1 prevails in the cuff 40. The valve 43 is opened at time t1, whereupon the pressure will drop steeply. The air within the system of flexible tubes 45 begins to flow, and a pressure drop occurs within the flexible tube leading to the cuff 40. The descending curve trace representative of this pressure drop is superimposed by oscillations 1 caused due to the fact that the air column knocks against the inner side of the flexible tube. At the time t2, at which the pressure p2 is measured, the valve 43 is closed again. As can be seen from FIG. 10, the pressure p2 does not correspond to the pressure within the cuff 40, but is reduced by the pressure drop within the flexible tube. During the valve closing operation, which is now carried out, the following dynamic process will take place: the flow is stopped; the pressure drop across the flexible tube 45 discontinues; the air column knocks again against the inner side of the flexible tube 45 whereby oscillations 2 will be caused, which change into a steady-state pressure p3.

In the course of the above process, thermal transients occur after closing of the valve in addition to the above-described acoustic transients caused by the fact that the air column knocks against the inner side of the flexible tube. These thermal transients are caused by the fact that, during the venting process, the expanding gas will cool down and reheat after closing of the valve at time t2, and this will result in a pressure rise of the pressure p3 to the final pressure p4, said pressure rise being superimposed in the form of an exponential function.

Similar effects are also produced when the cuff 40 is being filled.

These effects, viz. the pressure drop within the system of flexible tubes 45, the acoustic and thermal transients, are system dependent, i.e. they depend e.g. on the length of the tube and on the inside diameter of the tube, on the cuff volume of the cuff 40 and the material thereof, on the discharge characteristic of the valve 43 as well as on the capacity of the pressure generation device 41.

In order to sum up, it can be stated that the signal produced by the pressure sensor 42 of the kown blood pressure measuring device is not always representative of the filling state of the cuff, and that pressure changes detected by this pressure sensor do not necessarily mean that the filling state has changed.

In view of these discrepancies between the pressure signal, which is used in the known pressure measuring device for controlling the filling operation and the venting operation, and the actual filling state of the system, errors with respect to pressure adjustment occur in said known blood pressure measuring devices. When, for example, the transition from one pressure step to the next lower pressure step is controlled, the amount discharged is either too large or too small, whereupon a subsequent correction by renewed venting or additional pumping has to be carried out, and this, in turn, cannot be carried out precisely which means that an additional correction will possibly become necessary. This course of action will inevitably result in an extension of the overall measurement time.

In order to curb these problems arising with respect to the pressure control of the cuff pressure, different solution possibilites have been tried in the prior art.

There are, for example, blood pressure measuring devices working with a two-tube system. One of the tubes serves to connect the cuff to the pressure generation device at one side thereof and to the venting valve at the other side thereof. The other tube serves to connect the cuff to the pressure sensor. In view of the fact that no flow processes take place in the tube used for connecting the pressure sensor to the cuff, the above-described transients will not occur, and this will increase the measuring precision. Disadvantages of this solution are, however, the application, which, due to the size and the lack of flexibility of the bundle of tubes including the two tubes, is less convenient for the user as well as the additional expenditure entailed e.g. by the two couplings necessary at the cuff and the two couplings at the blood pressure measuring device.

A different solution attempt is to be seen in the measure of using no the longer pressure alone as a control criterion, but a controller having a control criterion relying on pressure alone and also a time control which is additionally introduced. Deviating from the above, it is also possible to use a combination of time control and pressure control.

When time control is effected, the pressure steps are controlled on the basis of the venting time, the opening times of the valve depending on the cuff volume and on the effective cuff pressure. This entails the problem that very specific venting times are necessary for each cuff volume and for each pressure level. Although these times can be filed in tables or expressed by functions after having been determined for a specific cuff size and a specific cuff pressure, said method works in a satisfactory manner only with respect to comparatively small pressure steps. The larger the pressure steps are, the greater will be the uncertainty with which the adjustment of the pressure value is achieved.

In all the known methods using the pressure signal as a primary control criterion, pressure fluctuations caused by artifacts may have the effect that, upon determining the pressure level, a wrong opening time for the valve is determined, or that, due to pressure fluctuations caused by artifacts, amounts of air which are larger or smaller than the intended amounts escape during the opening time so that, after closing of the valve, the desired pressure will not be obtained.

In all known blood pressure measuring devices, specific parameters of components of the respective device are used as a basis for determining time-dependent pressure control characteristics, said parameters being e.g. the cuff size, the capacity of the pump, the discharge characteristic of the valve, etc. If these parameters change, a change in the pressure variation per unit time will occur, and this, in turn, will result in an incorrect determination of the cuff size.

If the pressure signal is used as a control criterion, the controller must be based on predetermined parameters of the components. These parameters must be specified in an appropriate manner and produced such that they have the adequate tolerances, and this will entail higher production costs of the components. Changes in the mechanical or the pneumatic system, which entail changed parameters of the components, can only be carried out by a modified controller, whereby changes in the system will require a higher expenditure.

SUMMARY OF THE INVENTION

It is an object of the present invention to provide a blood pressure measuring device which permit a more precise adjustment of the cuff pressure.

It is another object of the present invention to provide a method of controlling the cuff pressure in a blood pressure measuring device, which permit a more precise adjustment of the cuff pressure.

In accordance with a first aspect of the invention, this object is achieved by a blood pressure measuring device comprising:

- a cuff which is adapted to be wrapped around a part of the patient's body;
- a pressure adjustment device for controlled filling and emptying of the cuff;
- a flow sensor which is arranged between said pressure adjustment device and said cuff;
- an integration means connected downstream of said flow sensor for producing a volume value; and
- a control means for controlling the pressure adjustment device on the basis of the volume value produced by said integration means as well as on the basis of at least one quantity representative of the pressure/volume dependence of the cuff pressure on the cuff-filling volume.

In a preferred embodiment of the invention, the blood pressure measuring device comprises:

- a cuff which is adapted to be wrapped around a part of the patient's body;
- a pressure generation device used for filling or for venting the cuff;
- a pressure sensor used for producing a pressure signal;
- a valve used for controlled emptying of the cuff;
- a flow sensor which is arranged between the cuff on the one side and the pressure generation device as well as the valve on the other side;
- an integration means connected downstream of said flow sensor and used for producing a volume value 4; and
- a control means which is connected to the valve, the pressure sensor and the integration means and which has a structural design of such a nature that it
- determines at least one quantity representative of the pressure/volume function on the basis of the pressure signal and the volume signal;

calculates a target volume value on the basis of a target pressure value for the respective pressure step and on the basis of said quantity representative of the pressure/volume function; and supplies to the valve a control signal for emptying the cuff until the actual volume value received from the integration means corresponds to the calculated target volume value.

In another preferred embodiment of the invention, the control means has a structural design of such a nature that it detects the gradient of the pressure/volume function on the basis of the respective actual volume values at two predetermined pressure values as the representative quantity.

In another preferred embodiment of the invention, the control means has a structural design of such a nature that it stores the pressure/volume function in the form of a plurality of actual volume values at a plurality of predetermined pressure values as a measured curve or measurement table.

In another preferred embodiment of the invention, the control means has a structural design of such a nature that it supplies a control signal to the pressure generation device so that said pressure generation device will fill the cuff until the pressure signal received from the pressure sensor reaches a maximum pressure value;

determines the quantity representative of the pressure/volume function;

calculates the target volume value for the respective next pressure step;

supplies to the valve the control signal for emptying the cuff until the actual volume value received from the integration means corresponds to the target volume value;

switches off the control signal for the valve so as to close said valve;

compares, when a predetermined period of time has elapsed after closing of the valve, the actual pressure with the target pressure of the present pressure step so as to detect a pressure deviation; and takes into account the thus detected pressure deviation upon determining the target volume value for the next pressure step.

In a further preferred embodiment of the invention, the flow sensor is provided with the following features:

a flow area of reduced-diameter located between the cuff on one side and the pressure generation device as well as the valve on the other side;

a differential pressure sensor having its pressure inputs connected to the ends of the reduced-diameter flow area; and a linearization means arranged downstream of said differential pressure sensor and having its output connected to the input of the integration means.

In accordance with a second aspect of the invention, this object is achieved by a method of controlling the cuff pressure in a blood pressure measuring device comprising:

a cuff which is adapted to be wrapped around a part of the patient's body;

a pressure adjustment device for controlled filling and emptying of the cuff;

a flow sensor which is arranged between said pressure adjustment device and said cuff;

an integration means connected downstream of said flow sensor for producing a volume value;

said pressure adjustment device being controlled on the basis of the volume value produced by said integration means as well as on the basis of at least one quantity representative of the pressure/volume dependence of the cuff pressure on the cuff-filling volume.

In accordance with a third aspect of the invention, this object is achieved by a method of controlling the cuff pressure in a blood pressure measuring device comprising:

a cuff which is adapted to be wrapped around a part of the patient's body;

a pressure generation device used for filling or for venting the cuff;

a pressure sensor used for producing a pressure signal;

a valve used for controlled emptying of the cuff;

a flow sensor which is arranged between the cuff on the one side and the pressure generation device as well as the valve on the other side;

an integration means connected downstream of said flow sensor and used for producing a volume value, and a control means which is connected to the valve, the pressure sensor and the integration means, said method including the following method steps:

determining at least one quantity representative of the pressure/volume function;

calculating a target volume value on the basis of a target pressure value for the respective pressure step; and opening the valve for emptying the cuff until the actual volume value received from the integration means corresponds to the calculated target volume value.

In a further preferred embodiment of the invention, the method includes the following method step:

calculating the gradient of the pressure/volume function on the basis of the respective actual volume values at two predetermined pressure values.

In a further preferred embodiment of the invention, the method includes the following method step:

storing in tabular form the pressure/volume function in the form of a plurality of actual volume values at a plurality of predetermined pressure values.

In a further preferred embodiment of the invention, the method includes the following method steps:

filling the cuff until the pressure signal received from the pressure sensor reaches a maximum pressure value;

determining the quantity representative of the pressure/volume function;

calculating the target volume value for the respective next pressure step;

emptying the cuff until the actual volume value received from the integration means corresponds to the target volume value;

closing the valve;

comparing, when a predetermined period of time has elapsed after closing of the valve, the actual pressure with the target pressure of the present pressure step so as to detect a pressure deviation; and taking into account the detected pressure deviation upon determining the target volume value for the next pressure step.

The blood pressure measuring device according to the present invention and the method of controlling the cuff pressure according to the present invention use a flow sensor, which is arranged between the pressure adjustment means on the one hand and the cuff on the other, as well as an integration means connected downstream of said flow sensor and used for producing a volume value on the basis of the flow sensor signal. The control means used for controlling the pressure adjustment means, which can consist e.g. of the pressure generation device and the valve, effects a control on the basis of the volume value produced by said integration means as well as on the basis of at least one quantity representative of the pressure/volume dependence of the cuff pressure on the cuff-filling volume or the cuff-discharge volume. This quantity can be the gradient of the volume related to the pressure or, if desired, the pressure/volume curve, which may be defined by a plurality of measuring points.

An advantage of the blood pressure measuring device according to the present invention as well as of the method according to the present invention is to be seen in the fact that an information on the actual filling state of the pneumatic system which can be used for the control is continuously available, said information being independent of dynamic transients and independent of artifacts.

The blood pressure measuring device according to the present invention and the method of controlling the cuff pressure effect rapid, precise adjustment of the respective pressures, and this will reduce the measuring time and make the blood pressure measuring device more convenient for the patient.

The blood pressure measuring device according to the present invention and the method of controlling the cuff pressure decouple the controller from parameters of the mechanical or the pneumatic system so that the control of the measuring process is rendered independent of component-specific parameters.

Furthermore, the device and the method according to the present invention permit an improvement of the safety standard, since the signal used for the control is independent of pressure measurements and since, consequently, incorrect interpretations of the cuff pressure are excluded. System errors can be recognized and qualified. Furthermore, the cuff size can be detected and continuously checked by the method according to the present invention.

During the cuff-filling or cuff-venting operation carried out in the course of the measurement of the blood pressure, the volume flow flowing into and/or out of the cuff is measured. The amount of air contained in the cuff is determined by means of integration, said amount of air constituting the instantaneous filling state of the cuff. Taking as a basis the amount of air and at least one quantity representative of the pressure/volume dependence of the cuff pressure on the volume, control of the cuff-filling or cuff-venting operation will be effected.

The static cuff pressure, which is uninfluenced by disturbances and which is required e.g. for measuring the oscillations in oscillometric blood pressure measurement processes at the respective pressure steps, and the amount of air contained in the cuff directly depend on one another, the type of dependence being, however, different from one system to the next. The blood pressure measuring device according to the present invention permits self-calibration on the basis of the fact that, in the cuff-filing operation, the volume value at a first predetermined pressure value and the volume value at a second predetermined pressure value are detected and that the gradient of the volume related to the pressure is then derived from these volume values.

Influences causing disturbances in known blood pressure measuring devices, such as pressure fluctuations caused by artifacts, do not exert any influence whatsoever when the blood pressure measuring device according to the present invention and the method of controlling the cuff pressure according to the present invention are used.

BRIEF DESCRIPTION OF THE DRAWINGS

In the following, preferred embodiments of the blood pressure measuring device according to the present invention and of the method of controlling the cuff pressure in a blood pressure measuring device according to the present invention will be explained in detail with reference to the drawings enclosed, in which.

DESCRIPTION OF THE PREFERRED EMBODIMENTS OF THE INVENTION

In the explanation of the preferred embodiments of the present invention with reference to FIG. 1 to 8, reference numerals corresponding to the reference numerals, chosen in FIG. 9 are used for designating identical or corresponding parts and components, respectively, so that a renewed explanation of the structure and of the function of the parts of the blood pressure measuring device can be dispensed with.

Figure 1:
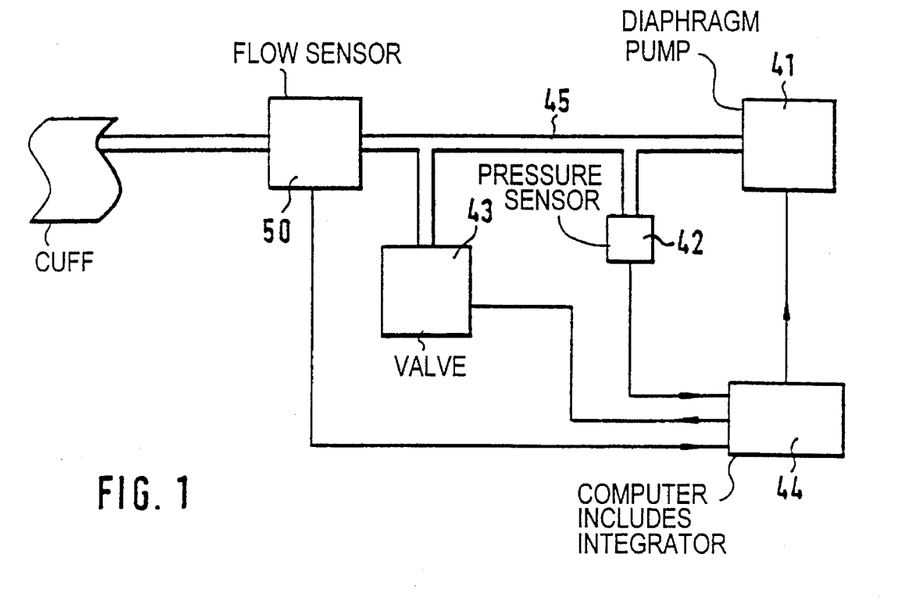
FIG. 1 is a block diagram of one embodiment of the blood pressure measuring device according to the present invention.

The preferred embodiment of the blood pressure measuring device according to the present invention shown in FIG. 1 comprises a cuff 40, which, via a system of flexible tubes 45, is connected to a pressure generation device 41 in the form of a diaphragm pump, to a pressure sensor 42 for producing a pressure signal, to a valve 43 for controlled emptying of the cuff, a flow sensor 50 being arranged between the cuff 40 on one side and the pressure generation device 41 and the valve 43 on the other side. The flow sensor 50, the valve 43, the pressure sensor 42 and the pressure generation device 41 are connected to a control unit 44 in the form of a computer unit.

The computer unit 44 calculates the integral of the output signal of the flow sensor 50 for generating a volume value, and, consequently, it simultaneously defines an integration means 63 for the output signal of the flow sensor 50.

The computing unit 44 determines at least one quantity representative of the pressure/volume function of the pneumatic system, and, as will still be explained hereinbelow, this can be done automatically during the cuff-filling operation. On the basis of this quantity representative of the pressure/volume function and on the basis of a target pressure value, which the computer unit 44 reads from a table for the respective pressure steps, the computing unit 44 derives a target volume value.

The computing unit 44 actuates the valve 43 long enough for maintaining an emptying process of the cuff 40 until the calculated target volume value corresponds to the actual volume value obtained by integration of the flow sensor output signal 50, whereupon the valve 43 is closed by switching off the control signal so as to maintain the pessure level of the respective pressure step.

A possible deviation of the target pressure for the respective pressure step, which is read out of the table, from the thus obtained actual pressure can be taken into account by the computer unit 44 when the discharge volume for obtaining the pressure of the next pressure step is determined.

In the preferred embodiment, the control unit 44 makes use of the gradient of the volume with respect to the pressure as the representative quantity, said gradient being determined by the difference between the respective actual volume values at two pedetermined pressure values. These predetermined pressure values are, for example, a pressure value of 20 mm Hg and a pressure value of 160 mm Hg, said pressure values lying, in accordance with a finding of the present invention, within a linear range of the pressure/volume function of the pneumatic system of the pressure measuring device. In other words, the pressure/volume function has an initial, non-linear characteristic representative of the filling of the initially slack cuff, whereas, from a specific basic pressure within the system, the integrated volume stream will essentially be linear with respect to the pressure rise.

Alternatively, it is possible that the computer unit 44 stores during the filling process a plurality of points of the pressure/volume function in the form of a plurality of actual volume values at a plurality of predetermined pressure values of the measured curve as a measurement table.

When the method according to the present invention and the blood pressure measuring device according to the present invention are used for oscillometric blood pressure measurements at stepped pressure levels, the computer unit 44 works such that it will first supply a control signal to the pressure generation device 41 so as to cause said pressure generation device to fill the cuff 40 until the pressure signal received from the pressure sensor reaches a pressure value po of e.g. 20 mm Hg, whereupon it will store the corresponding integrated volume value Vo. After additional filling of the cuff 40, the maximum pressure value pmax is reached, whereupon the corresponding volume value Vmax will be stored and the pressure generation device 41 will be switched off.

The gradient GD is determined on the basis of the volume difference Vmax-Vo related to the pressure difference pmax-po. This value is the quantity which is representative of the pressure/volume function.

The valve 43 will now be opened by the computer unit 44 until the actual volume value corresponds to the target volume value, whereupon the valve 43 will be closed by switching off the control signal.

When a predetermined period of time has elapsed after closing of the valve 43, the actual pressure will be compared with the target pressure of the presently relevant pressure step for detecting a possible pressure deviation, which will be taken into account when the target volume value for the next pressure step is determined.

Figure 2:
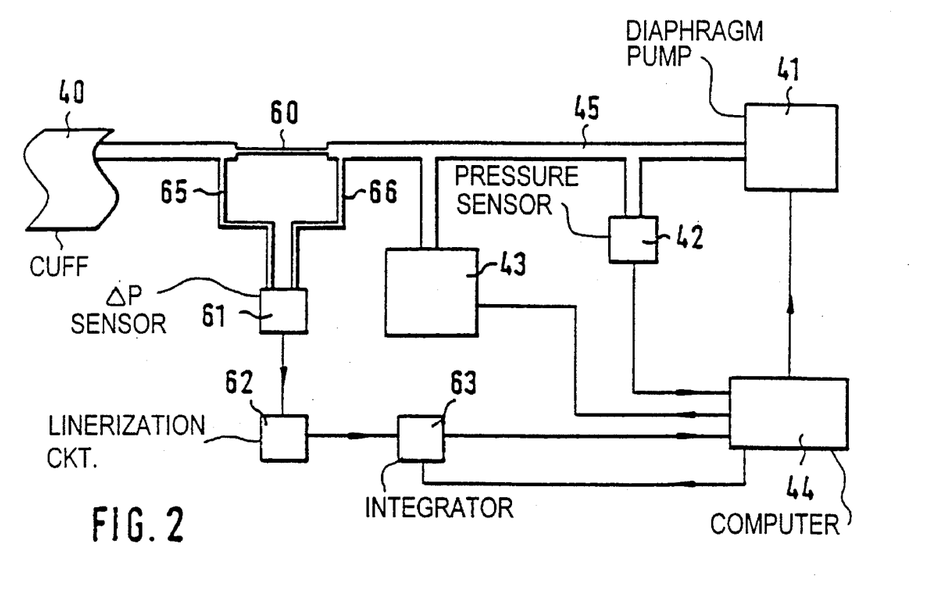
FIG. 2 is a block diagram of an additional embodiment of the blood pressure measuring device according to the present invention.

According to the modified embodiment of the blood pressuremeasuring device shown in FIG. 2, the flow sensor is defined by a tubular member 60, which has a reduced diameter in comparison with the inside diameter of the system of flexible tubes 45 and which is located between the cuff 40 on one side and the pressure generation device 41 and the valve 43 on the other side, a differential pressure sensor 61 having its pressure inputs 65, 66 connected to the ends of the reduced-diameter tubular member 60. The differential pressure sensor 61 is followed by a linearization circuit 62 whose outout is connected to an integration means 63 supplying the actual volume signal to a control means in the form of a computer unit 44. To the person skilled in the art it will be obvious that the integration means has been realized with the aid of hardware in this case, the realization in the field of software, which has been used in connection with the embodiment according to FIG. 1, being thus replaced by said hardware solution.

Figure 3:
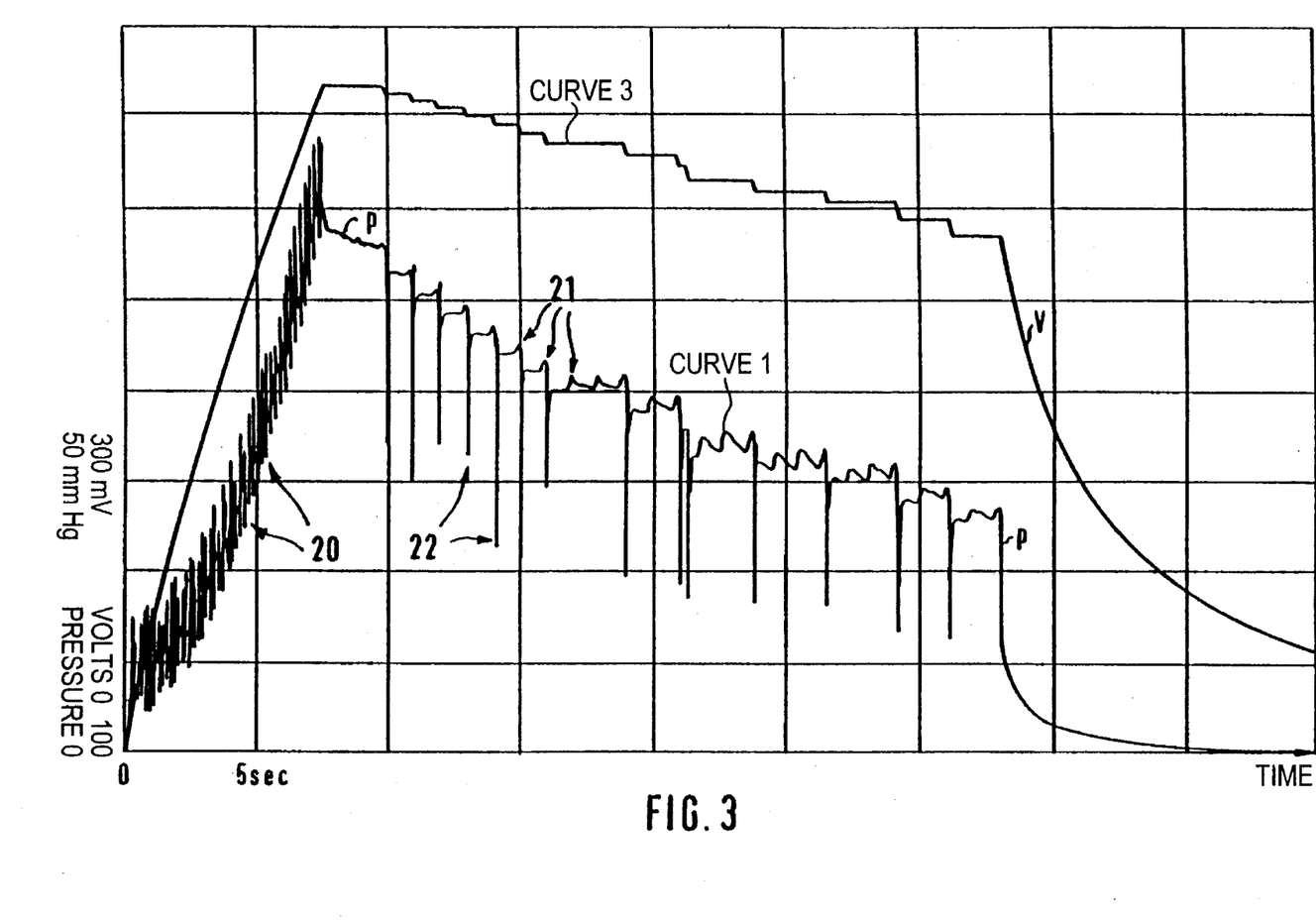
FIG. 3 is a plot of measured pressure variations and of the cuff filing state versus time.

FIG. 3 shows in the form of a curve 1 the variation with time of the pressure curve which is defined by the output signal of the pressure sensor 42. The curve shows pressure fluctuations 20 during the cuff-filling operation, which originate from the mode of operation of the diaphragm pump used as a pressure generation device. Said FIG. 3 additionally shows pulse oscillations 21 and overshoots as well as transients caused by the disturbance effects which have already been described; among said transients, especially the undershoots 22, which are caused by the pressure drop in the system of flexible tubes 45, catch the eye. Curve 3 shows the integrated flow signal, which is apparently free from component- or system-specific dynamic effects.

Figure 4:
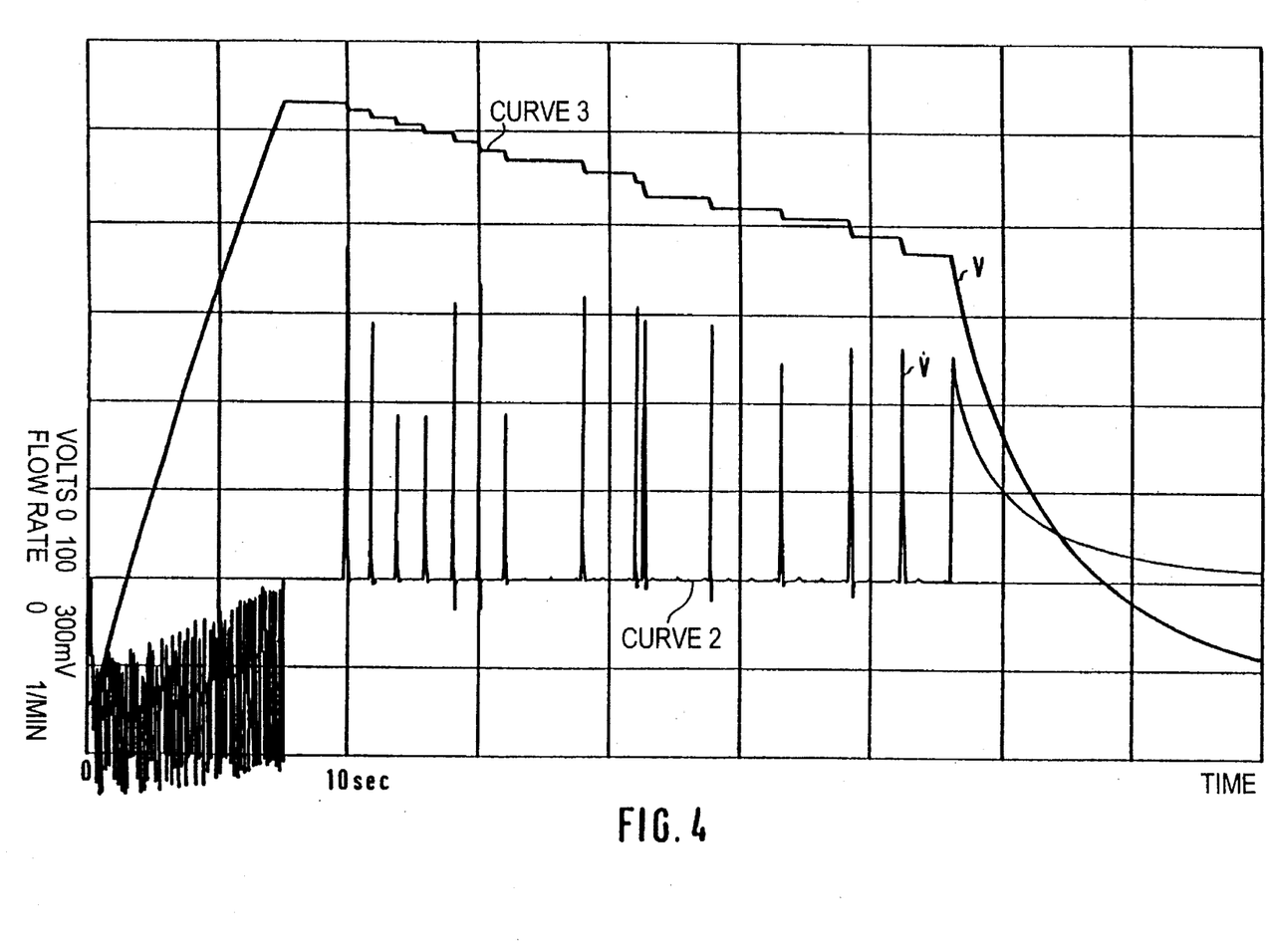
FIG. 4 is a plot of volume flow and of the cuff filing state versus time.

Also FIG. 4 shows in accordance with FIG. 3 the characteristic of the integrated flow signal as curve 3 as well as the characteristic of the volume stream as curve 2. It is specially emphasized that the zero point of the volume stream curve is displaced by two divisions on the ordinate. The opposite flow directions occurring during the initial filling operation and during the subsequent venting operation are visible in this figure. During the filling operation, the non-continuous supply mode of operation of the diaphragm pump can be seen. During the venting operation, the polarity of the flow signal is reversed due to the fact that the direction of flow has been reversed.

Figure 5:
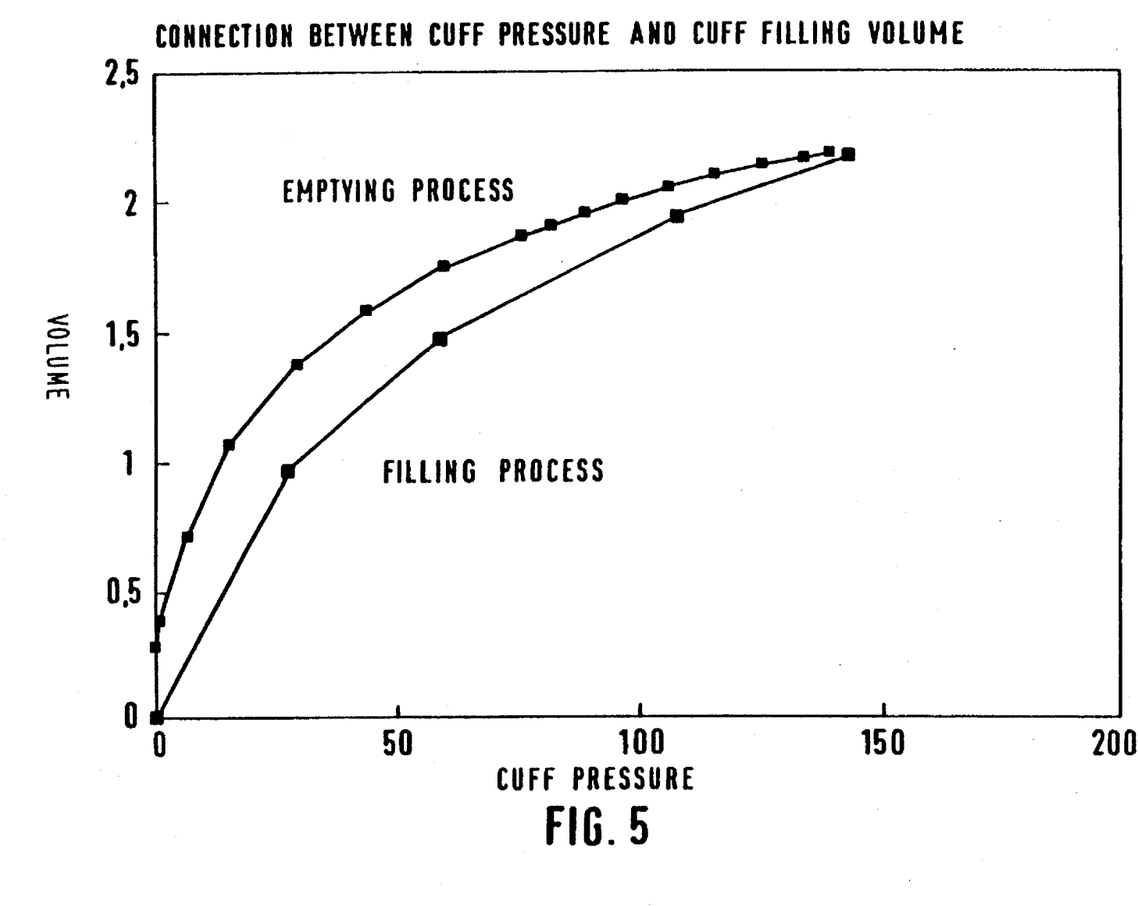
FIG. 5 is a plot of the connection between the cuff pressure and the cuff-filing state determined by integration of the volume flow.

FIG. 5 shows the connection between the cuff pressure and the volume during the cuff-filling operation as well as during the cuff-emptying operation. As has already been explained, the characteristics are neither linear nor congruent. The decisive factor in this respect is the thermal effect.

Figure 6:
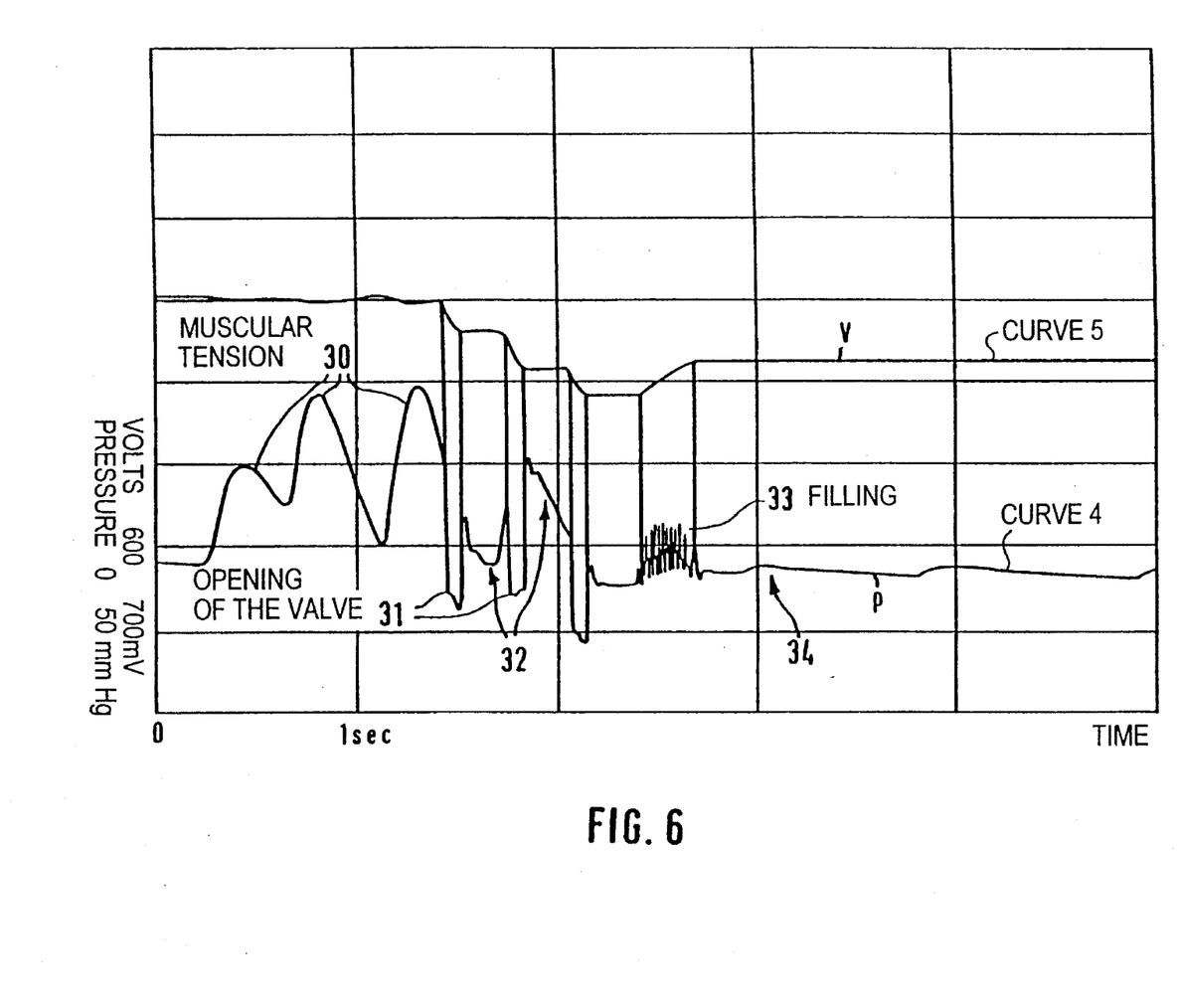
FIG. 6 is a plot of the variations with time of the cuff pressure and of the cuff-filing state determined by integration of the volume flow.

FIG. 6 shows the shape of the pressure curve as curve 4 as well as the shape of the integrated filling volume as curve 5 when extreme artifacts, which may be caused by movements of the patient or by muscular tension, occur.

FIG. 6 shows interferences with extreme pressure fluctuations of up to 100 mm Hg amplitude and pressure drops of approx. 50 mm Hg in the tube when the valve is opened. An examination of the pressure curve alone only shows several pressure rises 30, pressure drops 31 caused by opening of the valve, fluctuations 32 between the opening times and the refilling 33 of the cuff. It is, apparently, impossible to make any statements on the cuff-filling state or its variation on the basis of this signal.

FIG. 5, however, shows the integrated volume signal which is provided by the present invention and which can also be referred to as air balance. An examination of this signal will show immediately that the several pressure rises 30 do not alter the amount of air in the cuff. Being artifacts, this pressure rises are not taken into account. In the blood pressure measuring device according to the present invention, the discharge valve will not be opened in response to such pressure rises, but examination of the pressure characteristic will be continued until utilizable signals can be detected or until some other criterion stops the measuring of the blood pressure.

It can be seen that, during the valve opening times and shortly afterwards as well as during the filling operation, it is not possible to carry out an appropriate control of the filling state and of the venting operation on the basis of an examination of the pressure characteristic alone. The volume signal produced in accordance with the present invention, however, provides a reliable basis for system control during adjustment of the cuff pressure.

The control of the cuff-filling and cuff-venting operation which is carried out in accordance with the present invention on the basis of the integrated volume flow signal and on the basis of the air balance, respectively, effects a control on the basis of a signal representing the filling level of the pneumatic system irrespectively of dynamic flow processes and interferences, whereby the unerring precision in the control of the filling and venting operations is enhanced. Hence, the method according to the present invention permits a reduction of the measurement time, a selected controller being independent of specific parameters of structural components.

Furthermore, the reliability standard is increased, since, in addition to the pressure, a further signal exists on the basis of which specific states can be recognized and classified. It can, for example, be recognized whether parameters of certain components, such as the discharge characteristic of the valve or the supply amount of pressure generation change. Pressure rises caused by movements of the patient or pressure rises caused by unintentional filling due to an error can be differentiated.

Figure 7:
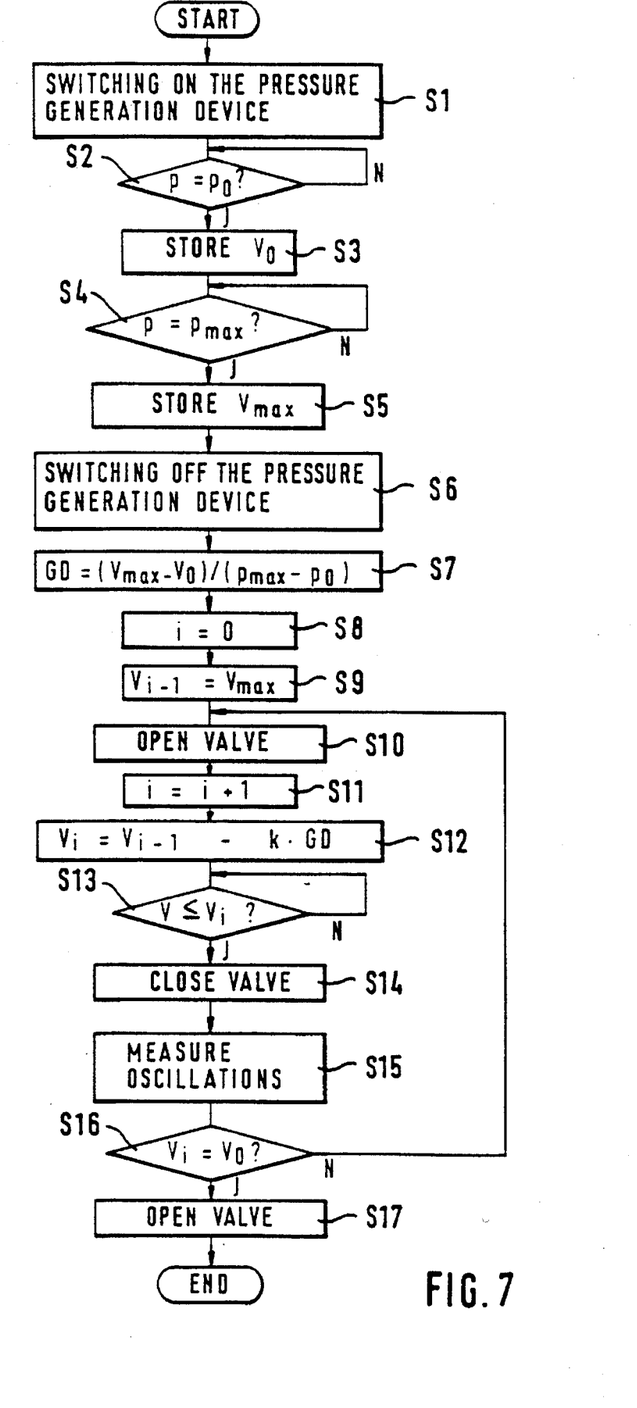
FIG. 7 and 8 are two control flow diagrams for carrying out the method of measuring the blood pressure according to the present invention.
Figure 8:
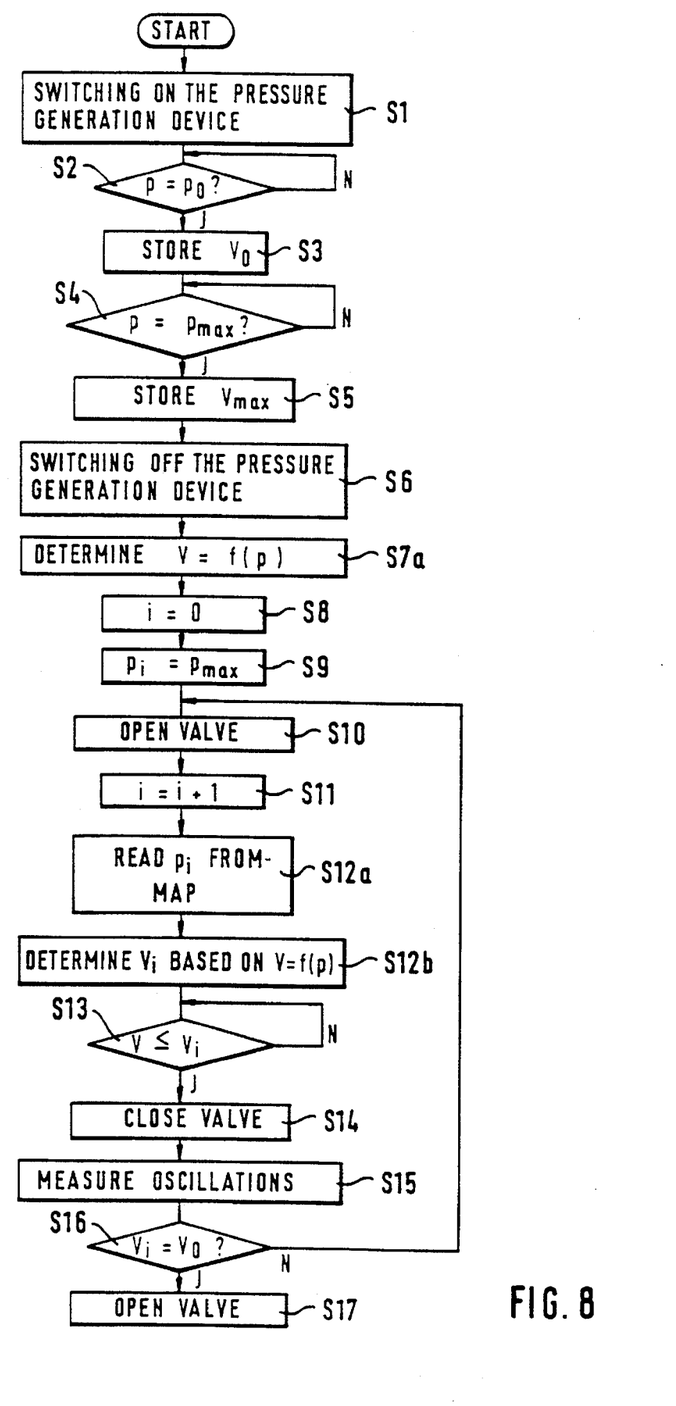

The flow diagrams of two controllers used for controlling the blood pressure measuring device according to FIG. 1 and 2 are shown in FIG. 7 and 8. To a person skilled in the art it will be obvious that the controllers can be implemented by a firmware within the computer unit 44.

When the system has been started, e.g. by actuation of a measurement button by the attending physician, the method begins with a first method step S1 in the course of which the pressure generation device 41 is switched on. In a second method step S2, it is examined whether the instantaneous pressure corresponds to a minimum pressure po of e.g. 20 mm Hg. Only if this condition is fulfilled, the respective volume value Vo, which corresponds to this pressure value po, will be stored. In the examination step S4 following said step S3, it will be compared whether the present pressure corresponds to a maximum pressure pmax of e.g. 180 mm Hg. As long as this condition is not fulfilled, this step will be repeated. When this condition has been fulfilled, the respective volume value Vmax, which is associated with said pressure value pmax, will be stored. Upon detecting the values po, Vo, pmax, and Vmax, the pump will preferably be switched off so as to prevent pressure drops in the tube which would corrupt the measurement.

In the sixth method step, the pressure generation device 41 is switched off. In a seventh method step S7, the gradient GD of volume changes with respect to pressure changes is determined on the basis of the above-mentioned measured values of volume and pressure.

Prior to venting of the system in several pressure steps, a loop counter i is set to zero in a step S8. In a step S9, a previous volume value Vi-1 is set to the value Vmax as an initial value.

In a subsequent method step S10, the valve 43 is opened. In the course of the eleventh step S11, the loop counter is incremented.

During the following step S12, the target volume value Vi is determined on the basis of the target volume value Vi-1 of the preceding pressure step, the gradient GD determined in the seventh step, the loop counter value i and a constant k.

In the course of the following thirteenth step of the examination method, it will be examined whether the present, integrated actual volume V is smaller than or equal to the target volume value Vi for the present pressure step. As long as this condition is not fulfilled, the examination of step S13 will be repeated. As soon as said condition has been fulfilled, the valve 43 will be closed during the following method step S14.

The measurement of the oscillation amplitudes induced in the cuff 40 by the artery can now be carried out in a fifteenth method step S15, if necessary after a short waiting time in which the tansients can decay.

In the next examination step S16, it will be examined whether the instantaneous volume Vi is equal to the volume Vo at the minimum pressure po. If this condition is not fulfilled, a return to program step S10 will take place. Otherwise, the valve 43 will be opened in the seventeenth method step S17 for emptying the cuff completely. The control program for one measuring cycle is now finished.

The deviating flow diagram according to FIG. 8, corresponds to the above-described process sequence with regard to the control steps S1 to S6, S8 to S11 and S13 to S17. However, instead of the determination of the gradient on the basis of previously measured values of pressure and volume in the seventh method step S7, the volume is here determined as a function of the pressure or it is filed point by point in a table.

Instead of calculating the target volume in the twelfth method step S12, a pressure value pi is, in a corresponding deviation, read from a table in a method step S12a, an associated target volume value being calculated on the basis of this pressure value or read from a table, if desired. The pressure value pi can be predetermined by a superordinate controller, e.g. the actual blood pressure measurement control procedure.

In step S7a shown in FIG. 8, it is also possible to use a table which is predetermined for the present system and which lays down the connection between the volume and the pressure for said system.

To the person skilled in the art it will be self-evident that the above-described determination of the pressure/volume connection by the system itself is, though preferable, not absolutely necessary.

Deviating still further from the embodiments described, hot-wire anemometers, laser or ultrasonic Doppler anemometers, impact pressure measurements or differential pressure measurements at orifices, nozzles or capillaries can be used as flow sensors.

Instead of the linearization means shown in FIG. 2, the linearization can be effected with the aid of programming by the computer unit 44. Also the integration by the integration means can be implemented by means of hardware as well as by means of software.

Furthermore, it is possible to switch on volume flow meters via suitable valves so that also very small volume flow movements can be detected. In this connection, volume flow meters with different capillaries are imaginable.

Volume flow meters can be arranged at various points of the pneumatic system described so that cases of failure, such as leakage, and damaged components, such as valves, pumps and control means, can be identified.

I claim:

1. A blood pressure measuring device comprising:
   a cuff which in use is wrapped around a part of the patient's body;
   a pressure adjustment device for controlled filling and emptying of the cuff;
   a flow sensor arranged between said pressure adjustment device and said cuff;
   an integration means connected to be responsive to said flow sensor for producing a volume value; and
   a control means for controlling the pressure adjustment device on the basis of the volume value produced by said integration means as well as on the basis of at least one quantity representative of a pressure/volume dependence of a cuff pressure on a cuff-filling volume.

2. A blood pressure measuring device according to claim 1, wherein the control means has a structural design of such a nature that it detects a gradient of the pressure/volume function on the basis of the respective actual volume values at two predetermined pressure values as the representative quantity.

3. A blood pressure measuring device according to claim 1, wherein the control means has a structural design of such a nature that it stores a pressure/volume function in the form of a plurality of actual volume values at a plurality of predetermined pressure values as a measured curve or measurement table.

4. A blood pressure measuring device according to claim 1, wherein the control means has a structural design of such a nature that it
   supplies a control signal to pressure generation device so that said pressure generation device fills the cuff until the pressure signal received from the pressure sensor reaches a maximum pressure value;
   determines the quantity representative of a pressure/volume function;
   calculates a target volume value for a respective next pressure step;
   supplies to a valve the control signal for emptying the cuff until the actual volume value received from the integration means corresponds to the target volume value;
   switches off the control signal for the valve so as to close said valve;
   compares, when a predetermined period of time has elapsed after closing of the valve, the actual pressure with a target pressure of the present pressure step so as to detect a pressure deviation; and
   takes into account the thus detected pressure deviation upon determining the target volume value for the next pressure step.

5. A blood pressure measuring device according to claim 1, wherein the flow sensor is provided with the following features:
   a flow area of reduced-diameter located between the cuff on one side and a pressure generation device as well as a valve on the other side;
   a differential pressure sensor having its pressure inputs connected to the ends of the reduced-diameter flow area; and
   a linearization means arranged downstream of said differential pressure sensor and having its output connected to the input of the integration means.

6. A blood pressure measuring device comprising:
   a cuff which in use is wrapped around a part of the patient's body;
   a pressure generation device for filling or for venting the cuff;
   a pressure sensor for producing a pressure signal;
   a valve for controlled emptying of the cuff;
   a flow sensor arranged between the cuff on the one side and the pressure generation device as well as the valve on the other side;
   an integration means connected to be responsive to said flow sensor for producing a volume value and
   a control means connected to the valve, the pressure sensor and the integration means and having a structural design of such a nature that it:
   (a) determines at least one quantity representative of a pressure/volume function on the basis of the pressure signal and the volume valve;
   (b) calculates a target volume value on the basis of a target pressure value for a respective pressure step and on the basis of said quantity representative of the pressure/volume function; and
   (c) supplies to the valve a control signal for emptying the cuff until an actual volume value received from the integration means corresponds to the calculated target volume value.

7. A blood pressure measuring device according to claim 6, wherein the control means has a structural design of such a nature that it detects a gradient of the pressure/volume function on the basis of the respective actual volume values at two predetermined pressure values as the representative quantity.

8. A blood pressure measuring device according to claim 6, wherein the control means has structural design of such a nature that it stores the pressure/volume function in the form of a plurality of actual volume values a plurality of predetermined pressure values as a measured curve or measurement table.

9. A blood pressure measuring device according to claim 6, wherein the control means has a structural design of such a nature that it
   supplies a control signal to the pressure generation device so that said pressure generation device will fill the cuff until the pressure signal received from the pressure sensor reaches a maximum pressure value;
   determines the quantity representative of a pressure/volume function;
   calculates the target volume value for a respective next pressure step;
   supplies the valve control signal for emptying the cuff until the actual volume value received from the integration means corresponds to the target volume value;
   switches off the control signal for the valve so as to close said valve;
   compares, when a predetermined period of time has elapsed after closing of the valve, an actual pressure with the target pressure of the present pressure step so as to detect a pressure deviation; and
   takes into account the thus detected pressure deviation upon determining the target volume value for the next pressure step.

10. A blood pressure measuring device according to claim 6, wherein the flow sensor is provided with the following features:
    a flow area of reduced-diameter located between the cuff on one side and the pressure generation device as well as the valve on the other side;

a differential pressure sensor having its pressure inputs connected to the ends of the reduced-diameter flow area; and a linearization means arranged downstream of said differential pressure sensor and having its output connected to the input of the integration means.

11. A method of controlling cuff pressure in a blood pressure measuring device to be used on a patient, the blood pressure measuring device including:

a cuff which in use is wrapped around a part of the patient's body;

a pressure adjustment device for controlled filling and emptying of the cuff;

a flow sensor connected between said pressure adjustment device and said cuff; and an integration means responsive to said flow sensor for producing a volume value;

the method comprising:
controlling said pressure adjustment device on the basis of the volume value produced by said integration means and on the basis of at least one quantity representative of a pressure/volume dependence of the cuff pressure on a cuff-filling volume.

12. A method according to claim 11 further including:

calculating a gradient of pressure/volume function on the basis of the respective actual volume values at two predetermined pressure values.

13. A method according to claim 11 further including:

storing in tabular form a pressure/volume function as plural actual volume values at a plurality of predetermined pressure values.

14. A method according to claim 11 further including:

filling the cuff until a pressure signal received from the pressure sensor reaches a maximum pressure value;

determining the quantity representative of a pressure/volume function;

calculating a target volume value for respective next pressure step;

emptying the cuff until an actual volume value received from the integration means corresponds to the target volume value;

closing a valve;

comparing, when a predetermined period of time has elapsed after closing of the valve, the actual pressure with a target pressure of the present pressure step so as to detect a pressure deviation; and taking into account the detected pressure deviation upon determining the target volume value for the next pressure step.

15. A method of controlling the cuff pressure in a blood pressure measuring device used on a patient, the blood pressure measuring device including:

a cuff which in use is wrapped around a part of the patient's body;

a pressure generation device for filling or for venting the cuff;

a pressure sensor for producing a pressure signal;

a valve for controlled emptying of the cuff;

a flow sensor connected on one side between the cuff and the pressure generation device as well as the valve on its other side;

an integration means responsive to said flow sensor used for producing a volume value, and a control means connected to the valve, the pressure sensor and the integration means, said method comprising the steps of:
determining at least one quantity representative of a pressure/volume function;

calculating a target volume value on the basis of a target pressure value for a respective pressure step; and opening the valve to empty the cuff until an actual volume value received from the integration means corresponds to the calculated target volume value.

16. A method according to claim 15 further including:

calculating a gradient of pressure/volume function on the basis of respective actual volume values at two predetermined pressure values.

17. A method according to claim 15 further including:

storing in tabular form the pressure/volume function as plural actual volume values at a plurality of predetermined pressure values.

18. A method according to claim 15 further including:

filling the cuff until the pressure signal received from the pressure sensor reaches a maximum pressure value;

determining the quantity representative of the pressure/volume function;

calculating the target volume value for the respective next pressure step;

emptying the cuff until the actual volume value received from the integration means corresponds to the target volume value;

closing the valve;

comparing, when a predetermined period of time has elapsed after closing of the valve, an actual pressure with the target pressure of the present pressure step so as to detect a pressure deviation; and taking into account the detected pressure deviation upon determining the target volume value for the next pressure step.

* * * * *